United States Patent
Becker et al.

[11] 3,954,442
[45] May 4, 1976

[54] HERBICIDAL COMPOSITIONS

[75] Inventors: Werner Becker, Frankfurt am Main; Peter Langelüddeke, Diedenbergen, Taunus; Heinrich Leditschke, Frankfurt am Main; Helmut Nahm; Friedhelm Schwerdtle, both of Kelkheim, Taunus, all of Germany

[73] Assignee: Hoechst Aktiengesellschaft, Frankfurt am Main, Germany

[22] Filed: May 11, 1973

[21] Appl. No.: 359,274

[30] Foreign Application Priority Data

May 17, 1972 Germany............................2223894

[52] U.S. Cl................................ 71/108; 71/98; 71/100; 71/109; 71/116; 71/118; 260/453 R; 260/455 R; 260/470; 260/471 A; 260/473 G; 260/501.12; 260/515 M; 260/515 A; 260/515 R; 260/516; 260/518 R; 260/518 A; 260/519; 260/520 C; 260/559 T; 260/559 A; 260/559 B

[51] Int. Cl.² ............................................ A01N 9/24
[58] Field of Search................... 71/108, 109, 116

[56] References Cited
UNITED STATES PATENTS

| | | | |
|---|---|---|---|
| 2,577,969 | 12/1951 | Jones | 71/109 |
| 2,759,965 | 8/1956 | Begin | 71/108 |
| 3,029,277 | 4/1962 | Metivier | 71/108 |

FOREIGN PATENTS OR APPLICATIONS

| | | | |
|---|---|---|---|
| 2,000,174 | 8/1969 | France | 260/473 IG |

OTHER PUBLICATIONS

Julia et al., "Growth Factors in Plants III, etc.," (1953), CA 48, pp. 5830–5831 (1954).
Mamaev et al., "Synthesis of Some Chlorophenoxy Derivatives," (1953), CA 47, p. 12287 (1953).

Primary Examiner—Glennon H. Hollrah
Attorney, Agent, or Firm—Curtis, Morris & Safford

[57] ABSTRACT

Compounds of the formula I

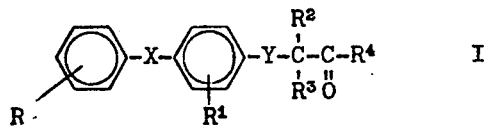

in which R represents hydrogen, halogen, alkyl having 1 to 4 carbon atoms, alkoxy and alkylthio having 1 to 4 carbon atoms, cyclohexyl, cyclopentyl, and phenyl, $R^1$ represents hydrogen, halogen, alkyl having 1 to 4 carbon atoms, and alkenyl having 2 to 4 carbon atoms, X and Y each are oxygen or sulfur, $R^2$ represents hydrogen, alkyl having 1 to 10 carbon atoms, alkoxyalkyl having 2 to 6 carbon atoms, alkyl-amino having 2 to 4 carbon atoms, or phenyl, $R^3$ represents hydrogen or alkyl having 1 to 4 carbon atoms, $R^4$ represents hydroxyl, —O-alkyl having 1 to 10 carbon atoms, —S-alkyl having 1 to 6 carbon atoms, —O—alkenyl having 2 to 4 carbon atoms, —O-cyclohexyl, —O-cyclopentyl, a phenoxy or phenylthio radical optionally substituted once or twice with halogen; —NH₂, —NH-alkyl having 1 to 4 carbon atoms, —N,N-dialkyl or

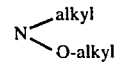

having 1 to 4 carbon atoms in each alkyl group, a —NH-phenyl radical substituted with halogen, —CF₃, —OCF₂CF₂H, or —COOCH₃, or —O-benzyl, or —NH-benzyl, or —S-benzyl, or —O-cat. wherein cat. stands for the cation of an inorganic or organic base, are valuable selective herbicides.

9 Claims, No Drawings

HERBICIDAL COMPOSITIONS

The present invention relates to herbicidal compositions.

In German Offenlegungsschrift 1,668,896 optionally substituted 4-phenoxy-phenoxy-alkane-carboxylic acids and derivatives thereof are disclosed and their action on the lipide and cholesterin metabolism is described. Compounds of the aforesaid class are also the object of German Offenlegungsschrift 2,136,828.

It has surprisingly been found that 4-phenoxy-phenoxy-alkane-carboxylic acids and the derivatives thereof exhibit an excellent selective herbicidal effect against weed grasses in crop plants.

The present invention provides herbicidal compositions containing a compound of the formula I

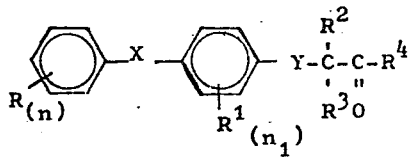

in which
R represents identical or different substituents selected from the group consisting of hydrogen, halogen, alkyl having 1 to 4 carbon atoms, alkoxy or alkylthio having 1 to 4 carbon atoms, cyclohexyl, cyclopentyl, and phenyl,
$R^1$ represents identical or different substituents selected from the group consisting of hydrogen, halogen, alkyl having 1 to 4 carbon atoms, and alkenyl having 2 to 4 carbon atoms,
X and Y each are oxygen or sulfur,
$n$ and $n_1$ stand for integers in the range of from 1 to 3,
$R^2$ represents hydrogen, alkyl having 1 to 10 carbon atoms, alkoxyalkyl having 2 to 6 carbon atoms, alkylamino having 2 to 4 carbon atoms, or phenyl,
$R^3$ represents hydrogen or alkyl having 1 to 4 carbon atoms,
$R^4$ represents hydroxyl, —O-alkyl having 1 to 10 carbon atoms, —S-alkyl having 1 to 6 carbon atoms, —O-alkenyl having 2 to 4 carbon atoms, —O-cyclohexyl, —O-cyclopentyl, phenoxy or phenylthio both optionally substituted once or twice with halogen, —NH$_2$, —NH-alkyl having 1 to 4 carbon atoms, N,N—di-alkyl or

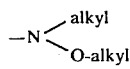

having 1 to 4 carbon atoms in each alkyl group, an —NH-phenyl radical substituted with halogen, —CF$_3$, —OCF$_2$CF$_2$H, or —COOCH$_3$; or —O-benzyl or —NH-benzyl or —S-benzyl or —O-cat. wherein cat stands for the cation of an inorganic or organic base
in combination with known formulation additives.

Another object of the invention are compounds of the formula I in which R, $R_1$, $R_2$, $R_3$, X, Y, $n$ and $n_1$ are as above
$R^4$ represents hydroxyl, —O-alkyl having 1 to 10 carbon atoms, —S-alkyl having 1 to 6 carbon atoms, —O-alkenyl having 2 to 4 carbon atoms, —O-cyclohexyl, —O-cyclopentyl, a phenoxy or phenylthio radical optionally substituted once or twice with halogen; —NH$_2$, —NH-alkyl having 1 to 4 carbon atoms, —N,N-dialkyl or

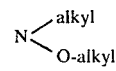

having 1 to 4 carbon atoms in each alkyl group, a —NH-phenyl radical substituted with halogen, —CF$_3$, —OCF$_2$CF$_2$H, or —COOCH$_3$, or —O-benzyl, or —NH-benzyl, or —S-benzyl.

In radicals $R^1$ to $R^4$ chlorine is the preferred halogen, methyl and ethyl are preferred as alkyl, and allyl as alkenyl.

The compositions according to the invention are selective in the pre-emergence as well as in the post-emergence process against weed grasses, even if used in high amounts, while broad leaved weeds are damaged to a small extent only. This special action on grasses contrasts with the action of chemically related growth-promoting compounds of the phenoxy-alkane-carboxylic acid series (for example 2,4-dichlorophenoxy-acetic acid (2,4-D) and 2,4-dichlorophenoxy-propionic acid (2,4-DP), the principal effect of which is the destruction of broad-leaved weeds. Simultaneously, the novel compositions do no harm to dicotyledonous (broad-leaved) crop plants.

Surprisingly the compositions according to the invention do not damage crop grasses such as rice, barley, eat, and wheat. Hence, the novel compositions can be used to combat weed grasses in cereals, i.e. crop grasses, which has been very difficult so far. Moreover, weed grasses can be efficiently controlled in dicotyledonous crop plants, for example in sugar beet, leguminosae, celery, clover, lucerne, melon, cucumber, and tobacco.

Owing to this special action against weed grasses, above all foxtail grass, bent and the like, the novel compositions are superior to a number of known herbicides such as alachlor, monolinuron, linuron, pyrazon, phenmedipham, sodium trichloroacetate, and prynachlor, when applied in fields strongly infested with weed grasses. Moreover, the amounts necessary for a complete destruction of the weed grasses are much smaller than with the above known herbicides. The amounts may vary within wide limits, for example in the range of from 0.1 to 10 kg of active ingredient per hectare, preferably 0.2 to 5 kg per hectare.

The compounds of formula I and the compositions containing them have a low toxicity against warm-blooded animals.

The compounds of formula I in which $R_4$ is hydroxy, their esters and salts with inorganic or organic bases are prepared by known methods as described in German Offenlegungsschrift 1,668,896, for example from 4-phenoxy-phenols of formula II by reaction with α-halocarboxylic acids of formula III or the esters or salts thereof.

Further 4-phenoxy-(thio)-phenoxy-(thio)-alkane-carboxylic acid derivatives are prepared by reacting the acid chlorides of formula V, obtained from the acid IV and an inorganic acid chloride such as thionyl chloride, with phenols, mercaptans, thiophenols, aliphatic amines, or anilines, represented in the following scheme by the abbreviation HR$^4$:

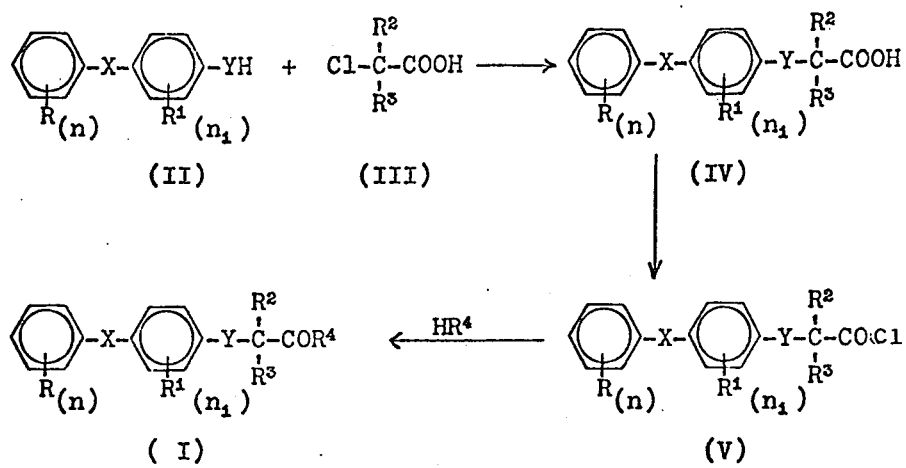

The compositions according to the invention contain the active ingredients of formula I generally in an amount of from 2 to 95 % by weight. They can be used in the form of wettable powders, emulsifiable concentrates, sprayable solutions, dusts, or granules, in admixture with the usual formulation auxiliaries.

Wettable powders are preparations that can be uniformly dispersed in water and contain, besides the active ingredient, a diluent or an inert substance, a wetting agent, for example polyoxethylated alkylphenols, polyoxethylated oleyl- or stearylamines, alkyl- or alkylphenyl sulfonates, and dispersing agents, for example the sodium salt of lignin-sulfonic acid, of 2,2′-dinaphthylmethane-6,6′-disulfonic acid, of dibutyl-sulfonic acid or sodium oleylmethyltauride.

Emulsion concentrates are obtained by dissolving the active ingredient in an organic solvent, for example butanol, cyclohexanone, dimethylformamide, xylene, or aromatic hydrocarbons having a higher boiling point. To obtain suspensions or emulsions in water having good properties, wetting agents as specified above are also added.

Dusting powders are obtained by grinding the active ingredient with finely divided, solid substances, for example talc, natural clays such as kaolin, bentonite, pyrophillite, or diatomaceous earths.

Spraying solutions commercially available as aerosol sprays contain the active ingredient dissolved in an organic solvent, and in addition thereto a propellant, for example a mixture of fluorochlorohydrocarbons.

Granules can be produced by atomizing the active ingredient on to an adsorptive, granulated inert material, or by applying concentrates of the active ingredient to the surface of a support, for example sand, kaolinite or a granulated inert material, with the aid of an adhesive, for example polyvinyl alcohol, the sodium salt of polyacrylic acid, or mineral oils. Alternatively, suitable active ingredients may be made into granules, if desired in admixture with fertilizers, in the manner commonly used for the manufacture of granulated fertilizers.

The commercial herbicidal perparations contain varying concentrations of the active ingredients. In wettable powders the concentration of active ingredient varies, for example, from about 10 to 95 %, the remainder being the above formulation additives. Emulsion concentrates contain about 10 to 80 % of active ingredient, while dusting powders mostly contain 5 to 20 % of active ingredient and sprayable solutions about 2 to 20 %. In the case of granules, the content of active ingredient partially depends on whether the active ingredient is liquid or solid and on the type of granulation auxiliary or filler used.

For application the commercial concentrates are optionally diluted in usual manner, the wettable powder or emulsifiable concentrate, for example with water. Dusts and granulated formulations as well as sprayable solutions are not diluted further with an inert substance before their application. The amount applied varies with the external conditions, such as temperature, humidity and the like. In general, about 0.015 to 0.25 gram and preferably about 0.03 to 0.12 gram of active ingredient per square meter are used.

The herbicides according to the present invention may be combined with other herbicides and soil insecticides.

Known herbicides suitable for combination with the novel compounds of the invention are, for example, the following compounds listed by their common or chemical names:

| | |
|---|---|
| urea derivatives | linuron, chloroxuron, monolinuron, fluometuron, diuron; |
| triazine derivatives | simazin, atrazin, ametryne, prometryne, desmetryne, methoprotryne; |
| uracil derivatives | lenacil, bromacil; |
| pyrazone derivatives | 1-phenyl-4-amino-5-chloropyridazone-(6); |
| growth-promoting preparations | 2,4-dichlorophenoxy-acetic acid, 4-chloro-2-methylphenoxy-acetic acid, 2,4,5-trichlorophenoxyacetic acid, 4-chloro-2-methylphenoxy-butyric acid, 2,3,6-trichloro-benzoic acid; |
| carbamic acid derivatives | barban, phenmedipham, triallate, diallate, vernolate, and 2-chloroallyl-N,N-diethyl-dithiocarbamate, swep; |
| dinitrophenol derivatives | dinitro-orthocresol, dinoseb, dinosebacetate |
| chlorinated aliphatic acids | trichloroacetic acid, dalapon |
| amides | diphenamide, N,N-diallyl-chloroacetamide |
| dipyridilium compounds | paraquat, diquat, morfamquat |

| | |
|---|---|
| anilides | N-(3,4-dichlorophenyl)-methacrylamide, propanil, solan, monalide, 2-chloro-2',6'-diethyl-N-(methoxymethyl)-acetanilide, propachlor |
| nitriles | dichlobenil, ioxynil |
| other preparations | flurenol, 3,4-dichloropropionanilide, trifluralin, bensulide, monosodium methyl arsonate, 4-trifluoro-methyl-2,4-dinitrodiphenyl ether. |

When the active ingredients according to the invention are mixed with fertilizers, preparations are obtained which simultaneously have a fertilizing and a herbicidal effect.

Formulation examples

EXAMPLE A

A wettable powder which is readily dispersible in water can be obtained by mixing
- 25 parts by weight of 4-(4-chlorophenoxy)-α-phenoxy-propionic acid as active ingredient
- 64 parts by weight of kaolin-containing quartz as inert substance
- 10 parts by weight of the potassium salt of lignin-sulfonic acid
- 1 part by weight of sodium oleylmethyl tauride as wetting and dispersing agent, and grinding the mixture obtained in a disk attrition mill.

EXAMPLE B

A dusting powder having good herbicidal properties can be obtained by mixing
- 10 parts by weight of 4-(4-chlorophenoxy)-α-phenoxypropionic acid as active ingredient
- 90 parts by weight of talcum as inert substance and grinding the mixture obtained in a cross-beater mill.

EXAMPLE C

An emulsifiable concentrate consists of
- 15 parts by weight of 4-(4-chlorophenoxy)-α-phenoxypropionic acid
- 75 parts by weight of cyclohexanone as solvent and
- 10 parts by weight of nonyl (ethoxy)$_{10}$ phenol as emulsifier.

The following examples illustrate the invention.

EXAMPLE 1

4-(4-Chlorophenoxy)-α-phenoxy-caproic acid ethyl ester

A solution of 64 g of 4-(4-chlorophenoxy)-phenol and 80 g of α-bromocaproic acid ethyl ester in 100 ml of butanone was refluxed for 10 hours together with 100 g of potassium carbonate. After separation from the inorganic salts by filtration, the filtrate was concentrated to dryness, the ester formed was taken up in methylene chloride, the solution was repeatedly extracted with water and the purified product was isolated by evaporating the organic solvent. It was further purified by distillation under reduced pressure. 52 Grams of 4-(4-chlorophenoxy)-α-phenoxy-caproic acid ethyl ester boiling at 223° – 225°C under 3 mm Hg were obtained.

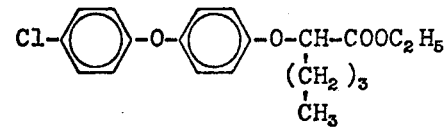

EXAMPLE 2

4-(4-Chlorophenoxy)-α-phenoxycaproic acid

52 Grams of the ester obtained as described in Example 1 were refluxed for 2 hours on the steam bath together with 300 ml of methanol and 30 ml of sodium hydroxide solution of 45 % strength. The excess solvent was removed under reduced pressure and the remaining sodium salt was dissolved in water. After acidification with concentrated hydrochloric acid, the acid separated first as an oil, then crystallized. It was recrystallized from 80 % acetic acid. 35 Grams of 4-(4-chlorophenoxy)-α-phenoxy-caproic acid melting at 94°C (corr.) were obtained.

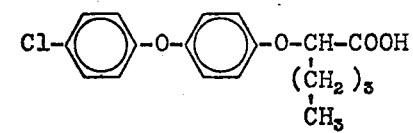

EXAMPLE 3

4-(4-Chlorophenoxy)-α-phenoxypropionic acid methyl amide

32 Grams of 4-(4-chlorophenoxy)-α-phenoxy-propionic acid chloride, prepared from 4-(4-chlorophenoxy)-α-phenoxypropionic acid (Example 5) and thionyl chloride, were dissolved in 150 ml of benzene and 7 grams of methyl amine were introduced at 15°C into the solution obtained. To complete the reaction the solution was stirred for 1 hour at 30°C, the precipitate formed was filtered off with suction, the benzenic solution was washed with water, dried over Na$_2$SO$_4$ and concentrated. The isolated crystals were recrystallized from petroleum ether. 28 Grams of 4-(4-chlorophenoxy)-α-phenoxypropionic acid methyl amide melting at 117° – 118°C were obtained.

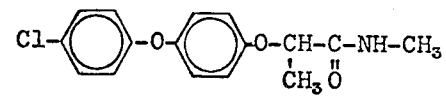

EXAMPLE 4

4-(4-chlorophenoxy)-α-phenoxy-propionic acid thioethyl ester

8 Grams of ethylmercaptan and 11 grams of pyridine were dissolved in 100 ml of toluene and 32 grams of 4-(4-chlorophenoxy)-α-phenoxy-propionic acid chloride were added dropwise at −5°C. The mixture was stirred for a further hour at room temperature. The precipitate was filtered off with suction, the toluenic solution was washed with water, dried over Na$_2$SO$_4$ and concentrated. The isolated crystals were recrystallized from petroleum ether. 29 Grams of 4-(4-chlorophenoxy)-α-phenoxypropionic acid thioethyl ester melting at 87° – 89°C were obtained.

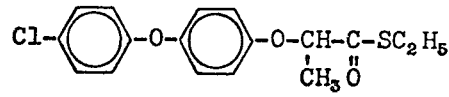

The following compounds were prepared in analogous manner:

Table

Compounds of the formula

| compound | R | X | R¹ | y | R² | R³ | R⁴ | boiling point b.p. melting point m.p. $n_D^{20}$ |
|---|---|---|---|---|---|---|---|---|
| 5 | 4-Cl | O | H | O | —CH₃ | H | —OH | m.p: 120°C |
| 6 | 4-Cl | O | H | O | —CH₃ | H | —OCH₃ | b.p.$_{0.15}$: 154°C |
| 7 | 4-Cl | O | H | O | —CH₃ | H | —OC₂H₅ | b.p.$_{0.15}$: 163°C |
| 8 | 4-Cl | O | H | O | —CH₃ | H | —O—C₃H₇(n) | b.p.$_{0.4}$: 182°C |
| 9 | 4-Cl | O | H | O | —CH₃ | H | —OCH(CH₃)₂ | b.p.$_{0.13}$: 170°C |
| 10 | 4-Cl | O | H | O | —CH₃ | H | —O(CH₂)₃—CH₃ | b.p.$_4$: 217°C |
| 11 | 4-Cl | O | H | O | —CH₃ | H | —O—CH₂—CH(CH₃)₂ | b.p.$_{0.15}$: 184°C |
| 12 | 4-Cl | O | H | O | —CH₃ | H | —O—(CH₂)₅—CH₃ | b.p.$_4$: 230°C |
| 13 | 4-Cl | O | H | O | —CH₃ | H | —O—CH₂—CH=CH₂ | $n_D^{20}$: 1.5527 |
| 14 | 4-Cl | O | H | O | —CH₃ | H | —O—CH₂—CCl₃ | $n_D^{20}$: 1.5601 |
| 15 | 4-Cl | O | H | O | —CH₃ | H | —S—C₃H₇(n) | $n_D^{20}$: 1.5702 |
| 16 | 4-Cl | O | H | O | —CH₃ | H | —O-cyclohexyl | b.p.$_1$: 226–232°C |
| 17 | 4-Cl | O | H | O | —CH₃ | H | —O-(methylcyclohexyl) | b.p.$_{0.5}$: 210°C |
| 18 | 4-Cl | O | H | O | —CH₃ | H | —O-cyclopentyl | b.p.$_{0.05}$: 176°C |
| 19 | 4-Cl | O | H | O | —CH₃ | H | —O—CH₂—C₆H₅ | b.p.$_{0.05}$: 158–161° |
| 20 | 4-Cl | O | H | O | —CH₃ | H | —O—(2,4-dichlorophenyl) | m.p.: 57–59°C |
| 21 | 4-Cl | O | H | O | —CH₃ | H | —S—C₆H₅ | m.p.: 66–68°C |
| 22 | 4-Cl | O | H | O | —CH₃ | H | —S—C₆H₄—Cl | m.p.: 64–66°C |
| 23 | 4-Cl | O | H | O | —CH₃ | H | —N(CH₃)₂ | m.p.: 61–64°C |
| 24 | 4-Cl | O | H | O | —CH₃ | H | —N(C₂H₅)₂ | m.p.: 61–62°C |
| 25 | 4-Cl | O | H | O | —CH₃ | H | —N(CH₃)(C₄H₉) | $n_D^{20}$: 1.5585 |
| 26 | 4-Cl | O | H | O | —CH₃ | H | —N(CH₃)(OCH₃) | m.p.: 87–88°C |
| 27 | 4-Cl | O | H | O | —CH₃ | H | —NH—C₆H₄—Cl | m.p.: 136–137°C |
| 28 | 4-Cl | O | H | O | —CH₃ | H | —NH—(dichlorophenyl) | m.p.: 121–123°C |
| 29 | 4-Cl | O | H | O | —CH₃ | H | —NH—C₆H₄—CF₃ | m.p.: 101–103°C |

Table-continued

Compounds of the formula

| compound | R | X | R¹ | y | R² | R³ | R⁴ | boiling point b.p. melting point m.p. $n_D^{20}$ |
|---|---|---|---|---|---|---|---|---|
| 30 | 4-Cl | O | H | O | —CH₃ | H | —NH-C₆H₄-OCF₂—CF₂H | m.p.: 103–105°C |
| 31 | 4-Cl | O | H | O | —CH₃ | H | —NH-C₆H₄-COOCH₃ | m.p.: 138°C |
| 32 | 4-Cl | O | H | O | —CH₃ | H | —O⁻Na⁺ | — |
| 33 | 4-Cl | O | H | O | —CH₃ | H | —O⁻K⁺ | — |
| 34 | 4-Cl | O | H | O | —CH₃ | —CH₃ | —OC₂H₅ | b.p.: 202–205°C |
| 35 | 4-Cl | O | H | O | —CH₃ | —CH₃ | —O(CH₂)₃—CH₃ | b.p.: 204–212°C |
| 36 | 4-Cl | O | H | O | —(CH₂)₅—CH₃ | H | —OH | m.p.: 70°C |
| 37 | 4-Cl | O | H | O | —(CH₂)₅—CH₃ | H | —OC₂H₅ | b.p.₄: 244°C |
| 38 | 4-Cl | O | H | O | —(CH₂)₇—CH₃ | H | —OH | b.p.: 66°C |
| 39 | 4-Cl | O | H | O | —(CH₂)₇—CH₃ | H | —OC₂H₅ | b.p.₃: 249–250°C |
| 40 | 4-Cl | O | H | O | —(CH₂)₉—CH₃ | H | —OH | m.p.: 64°C |
| 41 | 4-Cl | O | H | O | —(CH₂)₉—CH₃ | H | —OC₂H₅ | b.p.₀.₀₅: 220–230°C |
| 42 | 4-Cl | O | H | O | —(CH₂)₂—NH₂ | H | —OH | m.p.: 200°C (decomp.) |
| 43 | 4-Cl | O | 2-CH₂—CH=CH₂ | O | —CH₃ | H | —OC₂H₅ | b.p.₅: 210–230°C |
| 44 | 4-Cl | O | 2-CH₂—CH=CH₂ | O | —CH₃ | H | —O⁻H₂N⁺—(Ph)₂ | m.p.: 173°C |
| 45 | 4-Cl | O | H | O | —C₆H₅ | H | —OH | m.p.: 136°C |
| 46 | 4-Cl | O | H | O | H | H | —OH | m.p.: 166°C |
| 47 | 4-Cl | S | H | O | —CH₃ | H | —OH | — |
| 48 | 4-Cl | O | H | S | —CH₃ | H | —OH | m.p.: 110°C |
| 49 | 4-Cl | O | H | S | —C₂H₅ | H | —O⁻H₃N⁺—Benzyl | m.p.: 118°C |
| 50 | 2,4-Cl | O | H | O | H | H | —OH | m.p.: 112°C |
| 51 | 2,4-Cl | O | H | O | —CH₃ | H | —OC₂H₅ | b.p.₂: 217–219°C |
| 52 | 2,4-Cl | O | H | O | —CH₃ | H | —O—CH₂—CH(CH₃)₂ | b.p.₀.₁₂: 180–185°C |
| 53 | 2,4-Cl | O | H | O | —(CH₂)₂—NH₂ | H | —OH | m.p.: 200°C (decomp.) |
| 54 | 2,4-Cl | O | H | O | —C₆H₅ | H | —OH | m.p.: 118°C |
| 55 | 4-Cl | S | H | S | —CH₃ | H | —OH | — |
| 56 | 2,4-Cl | O | H | O | H | H | —OH | m.p.: 189–190°C |
| 57 | 2,4-Cl | S | H | O | —CH₃ | H | —OH | — |
| 58 | 2,4-Cl | S | H | S | H | H | —OH | — |
| 59 | 3,4-Cl | O | H | O | —CH₃ | H | —OCH(CH₃)₂ | b.p.₀.₀₄: 182–185°C |
| 60 | 3,5-Cl | O | H | O | —CH₃ | H | —OH | m.p.: 131°C |
| 61 | 4-F | O | H | O | H | H | —OH | m.p.: 152°C |
| 62 | 4-F | O | H | O | —CH₃ | H | —OH | m.p.: 129°C |
| 63 | 4-F | O | H | O | —C₂H₅ | H | —OH | m.p.: 77°C |
| 64 | 4-Br | O | H | O | H | H | —OH | m.p.: 147°C |
| 65 | 4-Br | O | H | O | —CH₃ | H | —O⁻Na⁺ | — |
| 66 | 4-J | O | H | O | H | H | —OH | m.p.: 148°C |
| 67 | 4-J | O | H | O | —CH₃ | H | —OH | m.p.: 170° |
| 68 | 4-J | O | H | O | —CH₃ | H | —OC₂H₅ | b.p.₃: 224–226°C |
| 69 | 4-J | O | H | O | —CH₃ | H | —O(CH₂)₃—CH₃ | b.p.₀.₁: 196°C |
| 70 | 4-J | O | H | O | —C₂H₅ | H | —OH | m.p.: 101°C |
| 71 | 4-J | O | H | O | —CH₂OCH₃ | H | —OH | m.p.: 70°C |
| 72 | 4-CH₃ | O | H | O | —CH₃ | H | —OH | m.p.: 91°C |
| 73 | 4-C(CH₃)₃ | O | H | O | —CH₃ | H | —OH | m.p.: 144°C |
| 74 | 4-C₆H₅ | O | H | O | —C₆H₅ | H | —OH | m.p.: 156°C |
| 75 | 3-CH₃,4-Cl | O | H | O | —C₆H₅ | H | —OH | m.p.: 114°C |

Table-continued

Compounds of the formula 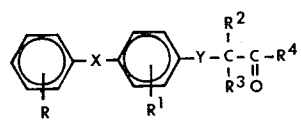

| compound | R | X | R¹ | y | R² | R³ | R⁴ | boiling point b.p. melting point m.p. $n_D^{20}$ |
|---|---|---|---|---|---|---|---|---|
| 76 | 3-CH₃;4-Cl | O | H | O | —(CH₂)₂—NH₂ | H | —OH | m.p.:220°C(decomp.) |
| 77 | 3,5-CH₃;4-Cl | O | H | O | —CH₃ | H | —OH | m.p.: 131°C |
| 78 | 3,5-CH₃;4-Cl | O | H | O | —CH₃ | H | —OC₂H₅ | b.p.₂:205–218°C |
| 79 | 2-Cyclopentyl; 4-Cl | O | H | O | —CH₃ | H | —O⁻H₃N⁺-Benzyl | m.p.: 138°C |
| 80 | 2-Cyclohexyl; 4-Cl | O | H | O | —CH₃ | H | —OC₂H₅ | b.p.₃: 243°C |
| 81 | 2-Cyclohexyl; 4-Cl | O | H | O | —CH₃ | H | —O⁻H₃N⁺—Benzyl | m.p.: 145°C |
| 82 | 4-OCH₃ | O | H | O | —CH₃ | H | —OH | m.p.: 92°C |
| 83 | 4-SCH₃ | O | H | O | —CH₃ | H | —OH | m.p.: 142°C |
| 84 | 4-SCH₃ | O | H | O | —C₂H₅ | H | —OH | m.p.: 80°C |
| 85 | H | O | H | O | —CH₃ | H | —OH | m.p.: 94–100°C |
| 86 | 2,4-Cl | O | H | O | —CH₃ | H | —OCH₃ | b.p. 0,1 162–163°C |
| 87 | 2,4-Cl | O | H | O | —CH₃ | H | —OC₃H₇(n) | b.p. 0,4 181–192°C |
| 88 | 2,4-Cl | O | H | O | —CH₃ | H | —OC₄H₉(n) | b.p. 0,3 188–190°C |
| 89 | 4-Br | O | H | O | —CH₃ | H | —OH | m.p.: 144–145°C |
| 90 | 4-Br | O | H | O | —CH₃ | H | —OCH₃ | b.p.₀,₃: 175–176°C |
| 91 | 4-Br | O | H | O | —CH₃ | H | —OC₂H₅ | b.p.₀,₁: 182–184°C |
| 92 | 4-Br | O | H | O | —CH₃ | H | —OC₃H₇(n) | b.p.₀,₃: 183–185°C |
| 93 | 4-Br | O | H | O | —CH₃ | H | —OC₃H₇(i) | b.p.₀,₃: 180–182°C |
| 94 | 4-Br | O | H | O | —CH₃ | H | —OC₄H₉(n) | b.p.₀,₃: 188–190°C |
| 95 | 4-Br | O | H | O | —CH₃ | H | —OC₄H₉(i) | b.p.₀,₃: 187–189°C |

APPLICATION EXAMPLES

EXAMPLE I

Seeds of weeds of different botanic families were sown in pots and the pots were placed in the greenhouse for about 3 weeks for germination. They were then sprayed with wettable powder formulations suspended in water and containing as active ingredient the compound of Example 5 or 50, respectively, in various concentrations. As comparative agents 2,4-D (2,4-dichlorophenoxy-acetic acid) and 2,4-DP (2-(2',4'-dichlorophenoxy)-propionic acid) were used in the same manner.

Other pots in which seeds of the same species of weeds had previously been sown were sprayed with the same spray liquors (pre-emergence treatment).

The results (and also the results of all following tables) were evaluated according to the following scheme in degree of damage in per cent:

| number | weeds | | | crop plants | | |
|---|---|---|---|---|---|---|
| 1 | 100 | | | 0 | | |
| 2 | 97.5 | to | <100 | 0 | to | 2.5 |
| 3 | 95 | to | <97.5 | >2.5 | to | 5 |
| 4 | 90 | to | <95 | >5 | to | 10 |
| 5 | 85 | to | <90 | >10 | to | 15 |
| 6 | 75 | to | <85 | >15 | to | 25 |
| 7 | 65 | to | <75 | >25 | to | 35 |
| 8 | 32.5 | to | <65 | >35 | to | 67.5 |
| 9 | 0 | to | <32.5 | >67.5 | to | 100 |

In this scheme number 4 is still considered an acceptable herbicidal effect in weeds and satisfactory preserving effect on crop plants (cf. Bolle Nachrichtenblatt des Deutschen Pflanzenschutzdienstes 16. 1964, pages 92 – 94).

The results of the following Table I show that in contrast to the compounds 2,4-D and 2,4-DP, the compounds of the invention did not exhibit or hardly exhibit an action against broad-leaf weeds, even if used in high amounts. Their special effect was restricted to species of the family of Graminaceae, shown by the examples of Lolium, Alopecurus and Echinochloa, against which 2,4-D and 2,4-DP were ineffective.

Table I

Greenhouse tests; effect against weeds and grasses; dosage in kilogram per hectare of active substance

| A. Post-emergence application | Nr. 5 | | Nr. 50 | | 2,4-D | | 2,4-DP | |
|---|---|---|---|---|---|---|---|---|
| | 2.5 | 0.62 | 2.5 | 0.62 | 2.5 | 0.62 | 2.5 | 0.62 |
| weeds: | | | | | | | | |
| Galium | 9 | 9 | 9 | 9 | 8 | 9 | 2 | 5 |
| Anthemis | 9 | 9 | 8 | 9 | 4 | 7 | 5 | 8 |
| Ipomoea | 8 | 9 | 9 | 9 | 1 | 3 | 3 | 6 |
| Sinapis | 8 | 9 | 9 | 9 | 1 | 1 | 1 | 1 |
| Amaranthus | 8 | 9 | 9 | 9 | 1 | 2 | 1 | 3 |
| weed grasses | | | | | | | | |
| Lolium | 4 | 7 | 3 | 8 | 9 | 9 | 9 | 9 |
| Alopecurus | 1 | 3 | 6 | 9 | 9 | 9 | 9 | 9 |
| Echinochloa | 1 | 3 | 1 | 2 | 9 | 9 | 9 | 9 |

| B. Pre-emergence application | Nr. 5 | | Nr. 50 | | 2,4-D | | 2,4-DP | |
|---|---|---|---|---|---|---|---|---|
| | 2.5 | 0.62 | 2.5 | 0.62 | 2.5 | 0.62 | 2.5 | 0.62 |
| weeds: | | | | | | | | |
| Galium | 9 | 9 | 9 | 9 | 8 | 9 | 2 | 6 |
| Anthemis | 8 | 9 | 9 | 9 | 8 | 8 | 5 | 9 |
| Ipomoea | 9 | 9 | 9 | 9 | 1 | 3 | 2 | 4 |
| Sinapis | 8 | 9 | 8 | 9 | 1 | 5 | 1 | 3 |
| Amaranthus | 8 | 9 | 8 | 9 | 2 | 6 | 1 | 5 |
| weed grasses: | | | | | | | | |
| Lolium | 1 | 1 | 2 | 3 | 8 | 9 | 9 | 9 |
| Alopecurus | 1 | 1 | 5 | 7 | 8 | 9 | 9 | 9 |
| Echinochloa | 1 | 1 | 1 | 1 | 9 | 9 | 9 | 9 |

EXAMPLE II

The compounds as used in Example I were sprayed in pre-emergence as well as in post-emergence application on different broad-loaf crop plants. The results of Table II show that compositions according to the invention, containing as active ingredient compound Nr. 5 and Nr. 50, fully spared the indicated broad-leaf crops even if applied in high dosages of 2.5 kilograms per hectare of active ingredient, whereas the same dosage of known phenoxy-fatty acid derivatives completely destroyed the crop plants when applied to the leaves (post-emergence application) and caused heavy damages in part when applied to the soil (pre-emergence application). Analogous results were obtained with the aforesaid preparations in other crops such as horse bean, kidney bean, vetch, clover, lucerne, sunflower, safflower, cucumber, pumpkin, flax, tomatoe, sugar melon, water melon, salad, tobacco, celery, and various types of cabbage.

Crop grasses such as barley, oat and wheat, were not damaged by the compounds of the invention when applied in the same manner.

EXAMPLE III

Seeds of some weed grasses and crop plants were sown in pots and after 3 weeks, in the 2- or 3-leaf-stage the plants were sprayed with suspensions of the compounds of the invention. The results obtained 4 weeks after the treatment are indicated in the following Table III.

Results similar to those with compound 10 of Table III were obtained with compounds 6, 7, 8, 9, 11, 16, 65, 77, and 78. The indicated results show that with post-emergence application the compounds of the invention exhibited a good and in part excellent effect in low dosages against certain weed grasses without damaging dicotyledonous crop plants, such as, pea, sugar beet, sunflower, or soybean.

Table II

Greenhouse test; effect on dicotelydonous crop plants, dosage 2.5 kilogram per hectare
PRE: pre-emergence application
POST: post-emergence application

| | Nr.5 | | Nr.50 | | 2,4-D | | 2,4-DP | |
|---|---|---|---|---|---|---|---|---|
| | PRE | POST | PRE | POST | PRE | POST | PRE | POST |
| sugar beet | 1 | 1 | 1 | 1 | 6 | 9 | 7 | 9 |
| rape | 1 | 1 | 1 | 1 | 7 | 9 | 9 | 9 |
| cucumber | 1 | 1 | 1 | 1 | 8 | 9 | 7 | 9 |
| carrot | 1 | 1 | 1 | 1 | 4 | 9 | 6 | 9 |
| cotton | 1 | 1 | 1 | 1 | 7 | 9 | 8 | 9 |
| soybean | 1 | 1 | 1 | 1 | 7 | 9 | 9 | 9 |
| pea | 1 | 1 | 1 | 1 | 7 | 9 | 8 | 9 |

Table III greenhouse test: effect on weed grasses and crop plants post-emergence application; dosage in kg/ha of active ingredient.

| | | weed grasses | | | crop plants | | | |
|---|---|---|---|---|---|---|---|---|
| compound | dosage | Alopecurus | Echinochloa | Digitaria | pea | sugar beet | sunflower | soybean |
| | 0.6 | 2 | 1 | 1 | 1 | 1 | 1 | 1 |

Table III-continued greenhouse test: effect on weed grasses and crop plants post-emergence application; dosage in kg/ha of active ingredient.

| compound | dosage | weed grasses | | | | crop plants | | |
|---|---|---|---|---|---|---|---|---|
| | | Alopecurus | Echinochloa | Digitaria | pea | sugar beet | sunflower | soybean |
| 5 | 0.3 | 5 | 1 | 1 | 1 | 1 | 1 | 1 |
| | 0.15 | 8 | 5 | 4 | 1 | 1 | 1 | 1 |
| | 0.6 | 1 | 1 | 1 | 2 | 3 | 1 | 1 |
| 17 | 0.3 | 3 | 2 | 1 | 1 | 1 | 1 | 1 |
| | 0.15 | 4 | 3 | 3 | 1 | 1 | 1 | 1 |
| | 0.6 | 1 | 1 | 1 | 3 | 4 | 1 | 2 |
| 10 | 0.3 | 3 | 1 | 1 | 1 | 1 | 1 | 1 |
| | 0.15 | 4 | 3 | 2 | 1 | 1 | 1 | 1 |
| | 0.6 | 1 | 1 | 1 | 2 | 4 | 3 | 1 |
| 12 | 0.3 | 3 | 1 | 1 | 1 | 1 | 1 | 1 |
| | 0.15 | 5 | 3 | 1 | 1 | 1 | 1 | 1 |
| | 0.6 | 8 | 1 | 1 | 1 | 1 | 1 | 1 |
| 50 | 0.3 | 8 | 3 | 4 | 1 | 1 | 1 | 1 |
| | 0.15 | 9 | 7 | 8 | 1 | 1 | 1 | 1 |
| | 0.15 | 7 | 1 | 2 | 1 | 1 | 1 | 1 |
| 67 | 0.075 | 9 | 5 | 6 | 1 | 1 | 1 | 1 |
| | 0.037 | 9 | 8 | 8 | 1 | 1 | 1 | 1 |
| | 0.15 | 1 | 1 | 1 | 1 | 2 | 1 | 1 |
| 68 | 0.075 | 4 | 1 | 2 | 1 | 1 | 1 | 1 |
| | 0.037 | 5 | 1 | 6 | 1 | 1 | 1 | 1 |
| | 0.15 | 2 | 1 | 1 | 1 | 4 | 1 | 1 |
| 69 | 0.075 | 3 | 1 | 3 | 1 | 1 | 1 | 1 |
| | 0.037 | 4 | 3 | 5 | 1 | 1 | 1 | 1 |
| | 0.6 | 6 | 1 | 1 | 2 | 2 | 1 | 1 |
| 51 | 0.3 | 8 | 1 | 1 | 1 | 1 | 1 | 1 |
| | 0.15 | 8 | 1 | 5 | 1 | 1 | 1 | 1 |

EXAMPLE IV

The effects of a number of other compounds of formula I against weed grasses in pre- and post-emergence application is shown in Table IV.

EXAMPLE V

About 4 weeks after germination a logarithmic spray test was preformed in a sugar beet field using two compounds of the invention. The results 5 weeks after application are indicated in Table V.

The two compounds considerably damaged Alopecurus (foxtail grass) but did no harm to the beet plants. Higher dosages (from 1 to 2 kg/ha) of active ingredient destroyed the weed grass. An infestation by foxtail grass could thus be eliminated after germination of the crop plant.

EXAMPLE VI

Seeds of foxtail grass and sugar beet were sown together in 20 cm deep containers. Part of the containers was treated on the same day with varying doses of compounds 5 and 67, respectively, according to the invention and of the comparative agents pyrazon (5-amino-4-chloro-2-phenyl-pyridazin-3(2H)-one) and sodium trichloroacetate, while the other part was sprayed three weeks after sowing. In the latter case, besides pyrazon, phenmedipham was used as comparative agent. (3-methoxycarbonylaminophenyl-N-(3'-methylphenyl)-carbamate).

Pyrazon is normally used to combat dicotyledonous weeds in pre- and post emergence application.

Phenmedipham is used to combat dicotyledonous weeds in post emergence application.

Table IV

Greenhouse test, effect on weed grasses pre- and post-emergence application (PRE - POST) dosage 2.5 kg/ha of active ingredient

| | Nr.5 PRE | Nr.62 PRE | Nr.82 PRE | Nr.83 PRE | Nr.72 PRE | Nr.70 PRE | Nr.70 POST | Nr. 71 PRE |
|---|---|---|---|---|---|---|---|---|
| Echinochloa | 1 | 4 | 2 | 3 | 1 | 4 | 8 | 3 |
| Lolium | 1 | 4 | 2 | 2 | 3 | 1 | 8 | 4 |
| Alopecurus | 1 | 4 | 1 | 3 | 2 | 1 | 1 | 3 |

Table V

Field test, effect on foxtail grass in sugar beet; Post-emergence application, dosage in kg/ha of active ingredient

| | Nr. 5 | | | | Nr.67 | | | |
|---|---|---|---|---|---|---|---|---|
| | 4 | 2 | 1 | 0.5 | 4 | 2 | 1 | 0.5 |
| weed grass | | | | | | | | |
| Alopecurus | 1 | 2 | 3 | 4–5 | 1 | 1 | 2 | 4 |
| crop plant | | | | | | | | |
| sugar beet | 1 | 1 | 1 | 1 | 1 | 1 | 1 | 1 |

Sodium trichloroacetate is used to control weed grasses in pre-emergence application.

The results summarized in Table VI evaluated about 4 weeks after the last treatment show that the compounds of the invention were very effective against foxtail grass both in pre-emergence and post-emergence application without damaging the sugar beet plants. The comparative agents pyrazon and phenmedipham were absolutely ineffective against foxtail grass, while sodium TCA exhibited an effect only in a very high dosage (15 kg/ha), but at the same time seriously damaged the sugar beet plants.

Table VI

Indoor vegetation test (natural atmospheric conditions) treatment against foxtail grass in sugar beet; dosage in kg/ha of active ingredient

|  | Nr. 5 | | | Nr. 67 | | | comparative agent I | II | III |
| --- | --- | --- | --- | --- | --- | --- | --- | --- | --- |
|  | 2.5 | 1.25 | 0.62 | 2.5 | 1.25 | 0.62 | 2.5 | 2.5 | 15.0 |
| pre-emergence application | | | | | | | | | |
| Alopecurus | 1 | 1 | 4 | 1 | 1 | 4 | 7 | — | 2 |
| sugar beet | 1 | 1 | 1 | 1 | 1 | 1 | 1 | — | 5 |
| post-emergence application | | | | | | | | | |
| Alopecurus | 1 | 3 | 4 | 3 | 4 | 6 | 8 | 8 | — |
| sugar beet | 1 | 1 | 1 | 1 | 1 | 1 | 2 | 1 | — | comparative agent   I = pyrazon
             II = phenmedipham
             III = sodium TCA

EXAMPLE VII

Maize and soybean were sown in a field strongly infested with weed grasses. After sowing the field was subdivided into sections each having a size of 20 m² and the sections were treated with different doses of compound 5 of the invention. As comparative agent alachlor (2-chloro-2',6'-diethyl-N-(methoxymethyl)-acetanilide) was used under the same conditions.

6 Weeks after treatment it could be seen that compound 5 had a distinctly better effect on the weed grasses than alachlor used in the same amounts (cf. Table VII). The crop plants were not damaged.

EXAMPLE VIII

Seeds of foxtail grass, kidney beans and peas were sown in 20 cm deep containers and at the day of sowing the surface of the soil was sprayed with aqueous suspensions contaning compounds of the invention as active ingredient. Monolinuron (N-4-chlorophenyl-N'-methyl-N'-methoxy urea) and linuron (N-3,4-dichlorophenyl-N'-methyl-N'-methoxy urea) were used as comparative agents.

4 Weeks after treatment it could be seen that compounds of the invention, for example Nrs. 5 and 67, did no harm to kidney beans and peas when applied in an amount of 0.62 kg/ha. Monolinuron frequently used in kidney beans satisfactorily controlled but did not destroy foxtail grass in a dose of 0.62 kg/ha. The kidney beans were seriously damaged at that dosage. Linuron which is often used in peas damaged the foxtail grass only slightly even when used in twice the amount (1.25 kg/ha) (cf. Table VIII)

Table VII

Field test, effect on weed grasses and crop plants pre-emergence application, dosage in kg/ha of active ingredient

|  | Nr. 5 | | | Alachlor | | |
| --- | --- | --- | --- | --- | --- | --- |
|  | 2 | 1 | 0.5 | 2 | 1 | 0.5 |
| weed grasses | | | | | | |
| Echinochloa | 1 | 2 | 3 | 3 | 6 | 9 |
| Setaria | 1 | 1 | 3 | 2 | 7 | 8 |
| Digitaria | 1 | 5 | 6 | 4 | 8 | 9 |
| crop plants | | | | | | |
| maize | 1 | 1 | 1 | 1 | 1 | 1 |
| soybean | 1 | 1 | 1 | 1 | 1 | 1 |

Table VIII

Indoor vegetation test (normal atmospheric conditions) pre-emergence application against foxtail grass in kidney beans and peas, dosage in kg/ha of active ingredient

|  | Nr. 5 | Nr. 67 | Monolinuron | | Linuron | |
| --- | --- | --- | --- | --- | --- | --- |
|  | 0.62 | 0.62 | 0.62 | 0.31 | 1.25 | 0.62 |
| Alopecurus | 1 | 1 | 4 | 9 | 8 | 9 |
| kidney bean | 1 | 1 | 6 | 1 | — | — |
| pea | 1 | 1 | — | — | 5 | 2 |

EXAMPLE IX

Cotton and soybeans were sown in a field strongly infested with weed grasses. 4 Weeks after sowing sections of 20 m² were treated with varying dosages of active ingredients of the invention. The results indicated in Table IX shows that the weed grasses were destroyed almost completely, partially with very low dosages (0.25 kg/ha). Even a manifold overdosages did not damage the crop plants cotton and soybean.

EXAMPLE X

In a greenhouse test the herbicidal effect and the tolerability by crop plants of compounds of the invention were tested in pre-emergence and post-emergence application. As comparative agent the known herbicide alachlor (cf. Table VII) was used. The results indicated in Table X show that in pre-emergence application compound 10 was superior to alachlor with the same dosage of active ingredient. Cotton, soybean, and peanut were spared while cotton was damaged by alachlor. In post-emergence application the compound of the invention likewise exhibited a distinct effect and did no harm to the crop plants, while alachlor was effective only in a higher dosage (0.62 kg/ha), but this effect was far from being satisfactory. Compounds Nrs. 6, 7, 8, 9, 11, and 12 had an analogous effect.

Table IX

Field test, effect on weed grasses and crop plants post-emergence application, dosage in kg/ha of active ingredient

|  | Nr. 5 | | | | Nr. 67 | | | |
| --- | --- | --- | --- | --- | --- | --- | --- | --- |
|  | 2 | 1 | 0.5 | 0.25 | 2 | 1 | 0.5 | 0.25 |
| weed grasses | | | | | | | | |
| Echinochloa | 1 | 1 | 3 | 4 | 1 | 1 | 1 | 2 |
| Digitaria | 1 | 3 | 4 | 6 | 1 | 1 | 1 | 1 |
| crop plants | | | | | | | | |
| cotton | 1 | 1 | 1 | 1 | 1 | 1 | 1 | 1 |
| soybean | 1 | 1 | 1 | 1 | 1 | 1 | 1 | 1 |

Table X

Greenhouse test, effect against weed grasses in cotton, soybean and peanut, dosage in kg/ha of active ingredient
PRE pre-emergence application POST post-emergence application

| | Nr.10 | | | | Alachlor | | | |
|---|---|---|---|---|---|---|---|---|
| | PRE | | POST | | PRE | | POST | |
| | 0.62 | 0.31 | 0.62 | 0.31 | 0.62 | 0.31 | 0.62 | 0.31 |
| weed grasses | | | | | | | | |
| *Digitaria sanguinalis* | 1 | 3 | 2 | 4 | 3 | 5 | 4 | 8 |
| *Echinochloa crus-galli* | 1 | 1 | 2 | 3 | 2 | 3 | 7 | 9 |
| *Echinochloa colonum* | 1 | 4 | 1 | 3 | 1 | 2 | 6 | 9 |
| *Eleusine indica* | 1 | 1 | 3 | 4 | 1 | 1 | 5 | 8 |
| *Leptochloa dubia* | 1 | 3 | 2 | 4 | 2 | 4 | 5 | 8 |
| *Panicum dichotomiflorum* | 1 | 1 | 2 | 5 | 2 | 5 | 4 | 8 |
| *Setaria faberii* | 1 | 4 | 1 | 5 | 1 | 5 | 6 | 9 |
| *Setaria viridis* | 1 | 4 | 2 | 4 | 1 | 4 | 6 | 9 |
| *Phalaris paradoxa* | 1 | 1 | 3 | 7 | 2 | 6 | 8 | 9 |
| crop plants | | | | | | | | |
| cotton | 1 | 1 | 1 | 1 | 5 | 1 | 3 | 1 |
| soybean | 1 | 1 | 1 | 1 | 1 | 1 | 1 | 1 |
| peanut | 1 | 1 | 1 | 1 | 2 | 1 | 2 | 1 |

EXAMPLE XI

Barley, wheat, oat, and rape were sown in spring side by side in a field infested with grass weeds. After germination of the crop plants sections of 20 m$^2$ were sprayed with aqueous suspension containing invention compounds in different concentrations. The results indicated in the following Table XI show that compounds 5 and 67 of the invention had an excellent effect on foxtail grass (Alopecurus) and bent (Apera) and that even a manifold overdose did no damage to the crop plants.

EXAMPLE XII

In a further field test maize, sunflower, peas, kidney beans, rape and carrots were sown and immediately after sowing sections of 20 m$^2$ were sprayed with liquors containing compounds of the invention in different concentrations. As comparative agent prynachlor (N-butin-(1 )-yl-(3)-α-chloroacetanilide) was used. 5 Weeks after treatment it could be seen that compounds Nrs. 5 and 67 of the invention had a good effect against germinating weed grasses, such as Echinochloa and Digitaria, and at the same time did no harm to the crop plants. The herbicidal effect of prynachlor was distinctly inferior.

Table XI

Field test, effect on weed grasses and crop plants post-emergence application, dosage in kg/ha of active ingredient

| | Nr. 5 | | | | Nr. 67 | | | |
|---|---|---|---|---|---|---|---|---|
| | 4 | 2 | 1 | 0.5 | 4 | 2 | 1 | 0.5 |
| weed grasses | | | | | | | | |
| *Alopecurus* | 1 | 1 | 2 | 3 | 1 | 1 | 3 | 4 |
| *Apera* | 1 | 1 | 1 | 1 | 1 | 1 | 1 | 2 |
| crop plants | | | | | | | | |
| barley | 1 | 1 | 1 | 1 | 1 | 1 | 1 | 1 |
| wheat | 1 | 1 | 1 | 1 | 1 | 1 | 1 | 1 |
| oat | 1 | 1 | 1 | 1 | 1 | 1 | 1 | 1 |
| rape | 1 | 1 | 1 | 1 | 1 | 1 | 1 | 1 |

Table XII

Field test, effect on weed grasses and crop plants pre-emergence application, dosage in kg/ha of active ingredient

| | Nr. 5 | | | Nr. 67 | | | Prynachlor | | |
|---|---|---|---|---|---|---|---|---|---|
| | 2 | 1 | 0.5 | 2 | 1 | 0.5 | 2 | 1 | 0.5 |
| weed grasses | | | | | | | | | |
| *Echinochloa* | 1 | 2 | 4 | 1 | 1 | 2 | 3 | 5 | 9 |
| *Digitaria* | 1 | 3 | 5 | 1 | 1 | 4 | 4 | 7 | 9 |
| crop plants | | | | | | | | | |
| maize | 1 | 1 | 1 | 1 | 1 | 1 | 1 | 1 | 1 |
| sunflower | 1 | 1 | 1 | 1 | 1 | 1 | 1 | 1 | 1 |
| pea | 1 | 1 | 1 | 1 | 1 | 1 | 1 | 1 | 1 |
| kidney bean | 1 | 1 | 1 | 1 | 1 | 1 | 1 | 1 | 1 |
| rape | 1 | 1 | 1 | 1 | 1 | 1 | 1 | 1 | 1 |
| carrot | 1 | 1 | 1 | 1 | 1 | 1 | 1 | 1 | 1 |

EXAMPLE XIII

4 Weeks old rice seedlings were planted in pots having a diameter of 15 cm into which seeds of *Echinochloa crus-galli* had previously been sown. One week after planting of the seedlings the pots were filled with water to a height of 1 cm above soil surface. At that time the Echinochloa plants had already germinated.

Aqueous suspensions containing compounds of the invention as active ingredient were added to the supernated water and the mixture was cautiously stirred. 4 Weeks after treatment the following result was observed. (cf. Table XIII)

Similar results were obtained with compounds Nrs. 6, 7, 8, 9, 12, 13, 16, 17, 50, 67, 68, and 69. The results demonstrate the selectivity of the claimed compounds in planted rice and their excellent effect on Echinochloa which is difficult to combat.

Table XIII

Effect on *Echinochloa* in planted rice, treatment after germination and planting, dosage in kg/ha of active ingredient

| compound Nr. | dosage | Echinochloa | rice |
|---|---|---|---|
| 5 | 0.6 | 1 | 2 |
| | 0.3 | 2 | 1 |
| | 0.15 | 7 | 1 |
| 10 | 0.6 | 1 | 2 |
| | 0.3 | 1 | 1 |
| | 0.15 | 2 | 1 |
| 11 | 0.6 | 1 | 2 |
| | 0.3 | 1 | 1 |
| | 0.15 | 1 | 1 |
| 51 | 0.6 | 1 | 3 |
| | 0.3 | 1 | 1 |
| | 0.15 | 3 | 1 |

EXAMPLE XIV

The weed grasses *Avena fatua* and *Alopecurus myosuroides* together with crop plants were sown in pots and after germination were sprayed with different dosages of compounds of the invention. The results indicated in Table XIV show that compounds Nrs. 86 and 68 of the invention had an excellent effect on both Avena and Alopecurus, with no or almost no damage to sugar beets and peas. Compound Nr. 86 did only little damage to wheat and barley, whereas the damage caused in these two crop plants by compound Nr. 68 was more pronounced. The comparative compound chlophenpropmethyl (β-[4-chlorophenyl]-α-chloropropionic acid methyl ester), which can be used for combating *Avena fatua* (wild oat) in various crops had an excellent effect on wild oat but was ineffective against Alopecurus (foxtail grass).

Compounds Nrs. 51, 52, 87, and 88 had an effect similar to that of compound 86, while compound Nr. 69 was similar to compound Nr. 68.

Table XIV

| compound Nr. | dosage | weed grasses | | sugar beet | pea | wheat | barley |
| --- | --- | --- | --- | --- | --- | --- | --- |
| | | Avena | Alopecurus | | | | |
| 86 | 2.5 | 1 | 1 | 1 | 3 | 4 | 5 |
| | 1.25 | 2 | 2 | 1 | 1 | 3 | 4 |
| | 0.62 | 3 | 4 | 1 | 1 | 1 | 1 |
| 68 | 2.5 | 3 | 1 | 2 | 1 | 8 | 8 |
| | 1.25 | 4 | 1 | 1 | 1 | 8 | 8 |
| | 0.62 | 5 | 1 | 1 | 1 | 7 | 7 |
| chlorphenprop-methyl | 2.5 | 1 | 8 | 3 | 4 | 3 | 2 |
| | 1.25 | 3 | 9 | 1 | 2 | 1 | 1 |

Effect on *Avena* and *Alopecurus* in various crop plants; treatment after germination, dosage in kg/ha of active ingredient

What is claimed is:

1. A method for combatting weed grasses in plantings of cereal and dicotylendenous crops which comprises applying to the planting site an effective concentration of a herbicidal composition containing as the active ingredient from about 2 to about 95 percent of a compound of the formula

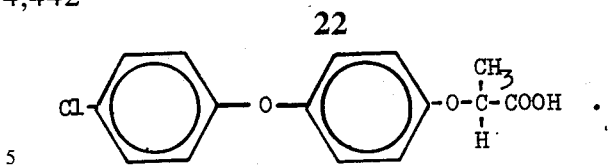

in which R represents identical or different substituents selected from the group consisting of halogen, alkyl of 1 to 4 carbon atoms, or methoxy; $R^1$ represents identical or different substituents selected from the group consisting of hydrogen, halogen, or methyl; $n$ and $n_1$ stand for integers from 1 to 3; and $R^4$ represents hyroxyl, —O-alkyl having 1 to 10 carbon atoms, —O-alkenyl having 2 to 4 carbon atoms, —O-cyclohexyl, —O-methylcyclohexyl, —O-cyclopentyl, phenoxy, phenoxy substituted once or twice with halogen, —O-benzyl, or —O-cat. wherein cat. stands for the cation of an inorganic or organic base, the balance being an inert herbicidal carrier.

2. A method as in claim 1 wherein said active ingredient is

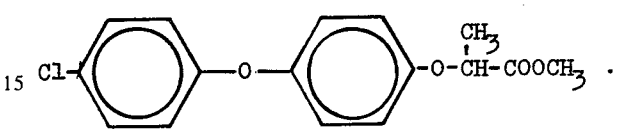

3. A method as in claim 1 wherein said active ingredient is

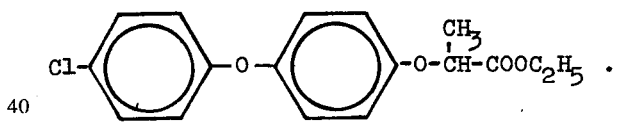

4. A method as in claim 1 wherein said active ingredient is

5. A method as in claim 1 wherein said active ingredient is

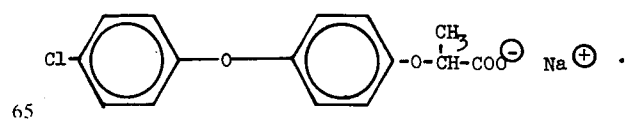

6. A method as in claim 1 wherein said active ingredient is

7. A method as in claim 1 wherein said active ingredient is

8. A method as in claim 1 wherein said active ingredient is
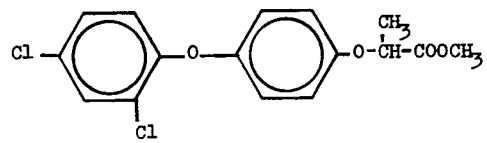
9. A method as in claim 1 wherein said active ingredient is
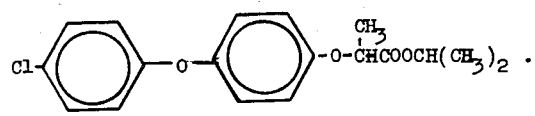
* * * * *